(12) United States Patent
Sasano et al.

(10) Patent No.: US 8,042,379 B2
(45) Date of Patent: Oct. 25, 2011

(54) METHOD OF ANALYZING ORGANIC CHEMICAL SUBSTANCES AND APPARATUS FOR ANALYSIS

(75) Inventors: Ryoichi Sasano, Wakayama (JP); Yutaka Nakanishi, Wakayama (JP)

(73) Assignee: AISTI Science Co., Ltd., Wakayama-shi (JP)

( * ) Notice: Subject to any disclaimer, the term of this patent is extended or adjusted under 35 U.S.C. 154(b) by 872 days.

(21) Appl. No.: 10/581,317

(22) PCT Filed: Dec. 3, 2004

(86) PCT No.: PCT/JP2004/018014
§ 371 (c)(1),
(2), (4) Date: Apr. 22, 2008

(87) PCT Pub. No.: WO2005/071398
PCT Pub. Date: Aug. 4, 2005

(65) Prior Publication Data
US 2008/0209983 A1 Sep. 4, 2008

(30) Foreign Application Priority Data

Dec. 5, 2003 (JP) ................................ 2003-407067
May 31, 2004 (JP) ................................ 2004-161061

(51) Int. Cl.
*G01N 1/28* (2006.01)
*G01N 30/84* (2006.01)
(52) U.S. Cl. ................................................... 73/23.41
(58) Field of Classification Search .................. 73/23.41
See application file for complete search history.

(56) References Cited

U.S. PATENT DOCUMENTS

| 4,935,145 | A  | * | 6/1990 | Cortes et al. ................... 210/656 |
| 5,236,593 | A  | * | 8/1993 | Cortes et al. ................... 210/656 |
| 5,522,988 | A  | * | 6/1996 | Cortes et al. ................. 210/198.2 |
| 6,354,145 | B1 | * | 3/2002 | Fransson et al. ............. 73/61.52 |
| 6,402,947 | B1 | * | 6/2002 | Altamirano et al. ........ 210/198.2 |
| 6,719,826 | B2 | * | 4/2004 | Sasano et al. ...................... 95/87 |

FOREIGN PATENT DOCUMENTS

| JP | 52-87088  | 7/1977  |
| JP | 59-38650  | 3/1984  |
| JP | 11-94812  | 4/1999  |
| JP | 11-258220 | 9/1999  |
| JP | 11-344477 | 12/1999 |

* cited by examiner

*Primary Examiner* — Daniel Larkin
(74) *Attorney, Agent, or Firm* — Kratz, Quintos & Hanson, LLP

(57) ABSTRACT

A combination of a liquid chromatograph and a gas chromatograph was a possible measure for improving precision in analyzing organic chemical substances. However, because elutes from liquid chromatoghaphies contain water and a highly polar solvent, injection thereof into a gas chromatograph has been impossible. Consequently, to develop an analytical method which realizes that combination and an apparatus thereof has been a subject. The method of the quantitative analysis comprises subjecting a sample for analysis prepared beforehand by extracting organic chemical substances from an assay sample to fractionation by a liquid chromatograph, continuously adsorbing a fractionated elute containing a substance to be determined onto a solid-phase cartridge while conducting the fractionation, eluting this substance, which has been adsorbed on the solid-phase cartridge, with an eluent, and transferring the elute to a storage chamber of a gas chromatograph.

20 Claims, 12 Drawing Sheets

Fig.6
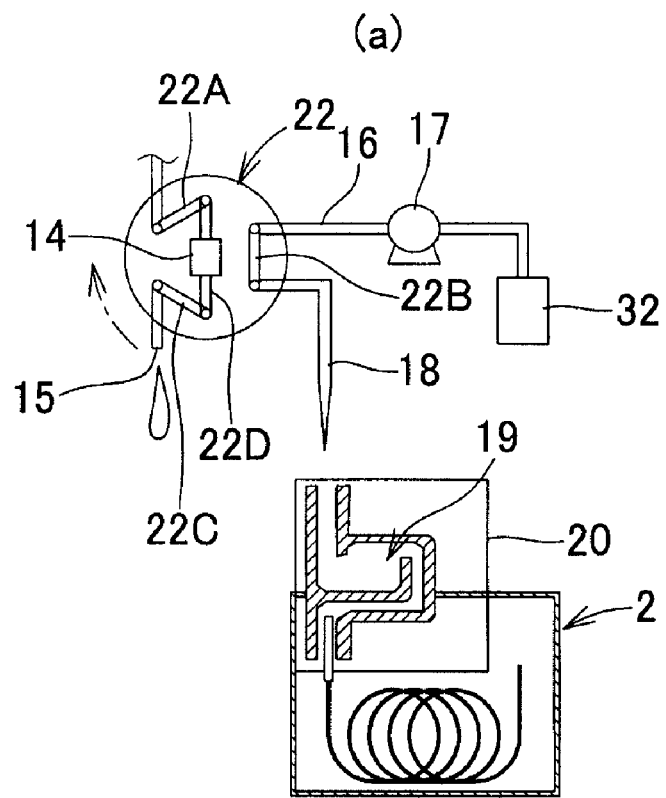
(a)
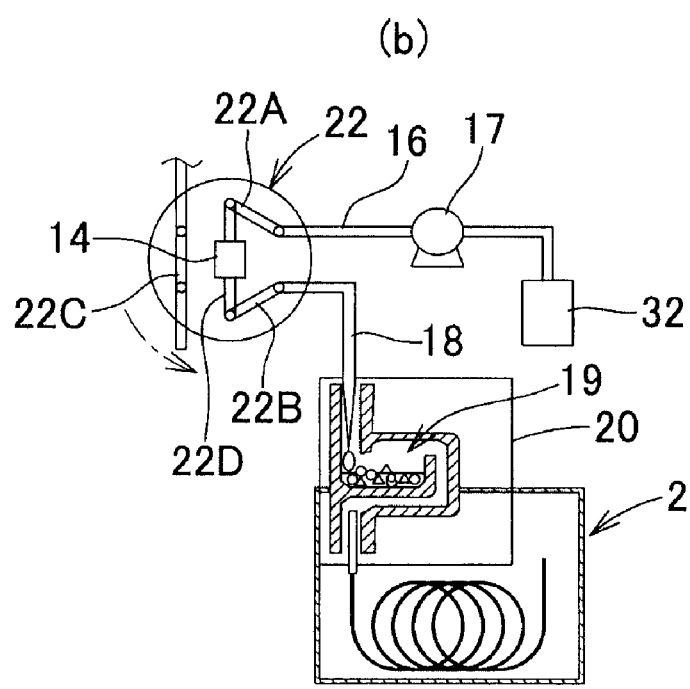
(b)

METHOD OF ANALYZING ORGANIC CHEMICAL SUBSTANCES AND APPARATUS FOR ANALYSIS

TECHNICAL FIELD

The present invention, in an analysis of organic chemical substances, relates to a method of analyzing an organic chemical substance and an apparatus for analysis where a sample for analysis prepared beforehand by extracting organic chemical substances from a target sample is subjected to fractionation by a liquid chromatography, and a fractionated analysis target substance thereby is quantitatively analyzed by a gas chromatography.

BACKGROUND ART

In an analysis of organic chemical substances, particularly agricultural chemicals, an analysis method by a liquid chromatography has been employed (for example, see Patent reference 1). Additionally, for an analysis of agricultural chemicals used in golf courses, a liquid chromatography has been also utilized (for example, see Patent reference 2). After that, a safety problem on residual agricultural chemicals adhered to farm products arose, which resulted in utilizing not only a liquid chromatography but also a gas chromatography. Further, methods have been proposed that a gas chromatography is combined with infrared absorption spectrum, and a microtrap is used as a pretreatment of a gas chromatography (for example, see Patent references 3 and 4). At the same time, as an environment problem becomes acknowledged, an analysis method of dioxin has been also studied (for example, see Patent reference 5).

Patent reference 1 Japanese Unexamined Patent Publication Hei 6-331618 (331618/1994)
Patent reference 2 Japanese Unexamined Patent Publication Hei 5-306998 (306998/1993)
Patent reference 3 Japanese Unexamined Patent Publication Hei 8-170941 (17094/1996)
Patent reference 4 Japanese Unexamined Patent Publication 2002-328121
Patent reference 5 Japanese Unexamined Patent Publication 2002-48688

DISCLOSURE OF THE INVENTION

Problems to be Solved by the Invention

The present invention was directed to analyzing organic chemical substances such as residual agricultural chemicals and endocrine disturbing chemicals, in consideration of a combination of a liquid chromatography and a gas chromatography for improving the precision, but because elutes from a liquid chromatography contain water, the elutes were not able to be injected directly into a gas chromatography. Consequently, it was aimed to realize a combination of a liquid chromatography and a gas chromatography and to analyze organic chemical substances quickly and precisely, and it was an object to develop an analysis method and an apparatus for analysis.

Means to Solve the Problems

As a result of diligent studies for solving the foregoing problems, the present inventors have reached to propose the present invention. Namely, in an analysis of organic chemical substances, a method of analyzing organic substances is characterized by: subjecting a sample for analysis prepared beforehand by extracting organic chemical substances from a target sample to fractionation by a liquid chromatograph to obtain a fractionated elute; adding a, different from the elute, solution to said fractionated elute containing an analysis target substance; continuously adsorbing said analysis target substance onto a solid-phase cartridge from the liquid chromatograph; and eluting the analysis target substance which has been adsorbed on said solid-phase cartridge with an eluent directly into a storage chamber of a gas chromatograph to analyze by gas chromatography. It is preferable that on eluting the analysis target substance which has been adsorbed on said solid-phase cartridge with an eluent directly into the storage chamber of a gas chromatograph, a derivatization reagent is dissolved in said eluent, and the resultant solution together with the analysis target substance is injected into a storage chamber of a gas chromatograph, so that, after the analysis target substance is derivatized in the storage chamber, the derivative is analyzed by gas chromatography. It is preferable that the analysis target substance which has been adsorbed on said solid-phase cartridge is eluted with an eluent, passed through a separate solid-phase cartridge whereby removing dirt, and then injected into a storage chamber of a gas chromatograph to be analyzed by gas chromatography. It is preferable that on eluting the analysis target substance which has been adsorbed on said solid-phase cartridge with an eluent, passing said eluent through a separate solid-phase cartridge and injecting an effluent with dirt having been removed into a storage chamber of a gas chromatograph, a derivatization reagent is dissolved in said effluent, and the resultant solution together with the analysis target substance is injected into a storage chamber of a gas chromatograph so that, after the analysis target substance is derivatized in the storage chamber, the derivative is analyzed by gas chromatography. It is particularly preferable that said analysis target substances are from 1 to 20 sorts.

The second invention is, in an analysis of organic chemical substances, a method of analyzing organic chemical substances characterized by: subjecting a sample for analysis prepared beforehand by extracting organic chemical substances from a target sample to fractionation by a liquid chromatograph to obtain a fractionated elute; passing said fractionated elute containing an analysis target substance through a solid-phase cartridge; continuously adsorbing said analysis target substance onto said solid-phase cartridge; and eluting the analysis target substance which has been adsorbed on said solid-phase cartridge with an eluent directly into a storage chamber of a gas chromatograph to analyze by gas chromatography. It is preferable that on eluting the analysis target substance which has been adsorbed on said solid-phase cartridge with an eluent directly into a storage chamber of a gas chromatograph, a derivatization reagent is dissolved in said eluent, injecting the resultant solution together with the analysis target substance into the storage chamber of the gas chromatograph so that, after the analysis target substance is derivatized in the storage chamber, the derivative is analyzed by a gas chromatography. It is preferable that the analysis target substance which has been adsorbed on said solid-phase cartridge is eluted with an eluent, passing said eluent through a separate solid-phase cartridge and injecting an effluent with dirt having been removed into the storage chamber of the gas chromatograph to be analyzed by gas chromatography. It is preferable that on eluting the analysis target substance which has been adsorbed on said solid-phase cartridge with an eluent, passing said eluent through a separate solid-phase cartridge whereby removing dirt, and injecting an effluent that dirt was removed from into a storage chamber of a gas chromatograph, a derivatization reagent is dissolved in said effluent, and the resultant solution together with the analysis target substance is injected into the storage chamber of the gas chromatograph so that, after the analysis target substance is derivatized in the storage chamber, the derivative is analyzed by gas chromatography. It is particularly preferable that said analysis target substances are from 1 to 20 sorts.

The third invention is an apparatus for analyzing organic chemical substances comprising: a liquid chromatograph where a sample for analysis prepared by extracting organic chemical substances contained in a target sample is introduced for fractionation; a first providing means for automatically providing a first solution being different from an elute based on an elution time of said analysis target substance to an elute containing an analysis target substance fractionated by the liquid chromatograph; a solid-phase cartridge for adsorbing the analysis target substance transferred by a mixed liquid of said first solution and the elute fractionated by the liquid chromatograph; a second providing means for automatically providing an eluent to elute the analysis target substance which has been adsorbed on the solid-phase cartridge; and a syringe needle connected to an exit of said solid-phase cartridge to introduce said eluted analysis target substance to a gas chromatograph. It is preferable that besides a first pathway to adsorb the analysis target substance transferred by a mixed liquid of said first solution and the elute fractionated by the liquid chromatograph onto the solid-phase cartridge, a second pathway is separately provided to elute the analysis target substance which has been adsorbed on the solid-phase cartridge and introduce to said gas chromatograph, and that said solid-phase cartridge is capable of freely being assembled and disassembled with each of two pathways respectively. It is preferable that a switching valve is provided to switch providing states into a first providing state for providing and adsorbing the analysis target substance transferred by a mixed liquid of said first solution and the elute fractionated by the liquid chromatograph onto said solid-phase cartridge, and into a second providing state for providing said eluent to said solid-phase cartridge to elute the analysis target substance which has been adsorbed on the solid-phase cartridge and introducing the same to said gas chromatograph. It is particularly preferable that said gas chromatograph is provided, inside its vaporizing chamber, with a storage chamber that is free from scavenger and is capable of temporarily storing the analysis target substance introduced from the syringe needle.

The fourth invention is an apparatus for analyzing organic chemical substances characterized by: a liquid chromatograph where a sample for analysis prepared by extracting organic chemical substances contained in a target sample is introduced for fractionation; a detecting means for detecting the analysis target substance transferred from the liquid chromatograph after being fractionated; an exhaust address switching valve for switching an exhaust address from an exhaust pathway side to a main pathway side based on a detected signal for the analysis target substance by the detecting means; a solid-phase cartridge provided in said main pathway to adsorb the analysis target substance transferred together with an elute being switched into the main pathway by said exhaust address switching valve; a providing means for providing an eluent for introducing the analysis target substance which has been adsorbed on said solid-phase cartridge into the gas chromatograph; and a syringe needle capable of moving up and down connected to the exit of said-phase cartridge to introduce the analysis target substance eluted together with said elute to a gas chromatograph. It is preferable that besides the first pathway to adsorb the analysis target substance transferred together with said elute onto said cartridge, a second pathway is separately provided to introduce the analysis target substance which has been adsorbed on said solid cartridge ane eluted with an eluent by said providing means to said gas chromatograph, and that said solid-phase cartridge can be freely assembled and disassembled with each of the two pathways respectively. It is preferable that a providing state switching valve is provided for the switching providing state into a first providing state to supply and adsorb the analysis target substance transferred together with said elute onto the solid-phase cartridge, and into a second providing state to supply said eluent to the solid-phase cartridge to elute the analysis target substance which has been adsorbed on said solid-phase cartridge and introduce into the gas chromatograph. It is particularly preferable that the gas chromatograph is provided, inside its vaporizing chamber, with a storage chamber that is free from scavenger and is capable of temporary storing the analysis target substance introduced from the syringe needle.

Effect of the Invention

The analysis method of the present invention is excellent in analyzing organic chemical substances including dirt with a high precision, in particular, most effective when organic chemical substances are from 1 to 20 sorts, and can analyze analysis target substances precisely and quickly.

According to the present invention, many sorts of organic chemical substances can be analyzed with a high precision, because a sample for analysis is fractionated continuously by a reverse phase liquid chromatography, and the elute is passed through a solid-phase cartridge to adsorb analysis target substances, thereby to supply the analysis target substances to a gas chromatograph (GC) from a liquid chromatograph (LC) without involving water and a highly polar solvent.

According to the present invention, because a syringe needle capable of moving up and down is connected to an exit of a solid-phase cartridge, the analysis target substance can be injected from the solid-phase cartridge to a gas chromatograph simply and without loss. Additionally, by using a gas chromatograph which is provided inside its vaporizing chamber with a storage chamber for temporary storage of an analysis target substance introduced from the syringe needle, the entire amount of elute from the solid-phase cartridge can be injected to the gas chromatograph. Further, since liquid chromatography as an analysis method constructed in a liquid chromatograph (LC)-gas chromatograph (GC) has a function of clean up, analysis can be carried out without pretreatment of clean up.

According to the present invention, on eluting analysis target substances adsorbed on a solid-phase cartridge with an eluent to inject directly into a storage chamber of a gas chromatograph, a derivatizion reagent is dissolved in the eluent, and the resultant solution together with the analysis target substances is injected into a storage chamber of the gas chromatograph so that, after the analysis target substance is derivated, the derivative can be analyzed by gas chromatography, which enables increasing the sorts of analysis target substances and enhance the precision of analysis.

According to the present invention, by providing a switching valve to switch a providing state into a first providing state for providing a first elute and into a second providing state for providing an eluent to a solid-phase cartridge, no operation is required to remove the solid-phase cartridge from a first pathway and install to a second pathway, which enables an analysis operation more rapidly.

BRIEF DESCRIPTION OF THE DRAWINGS

FIG. 6 is a magnified view of substantial parts in the apparatus for analysis shown in FIG. 5; (a) showing the first providing state for adsorbing an analysis target substance onto a solid-phase cartridge, and (b) showing the second providing state for eluting the absorbed analysis target substance to supply to a chromatograph.

DESCRIPTION OF NUMBER AND SYMBOL

Figure 1:
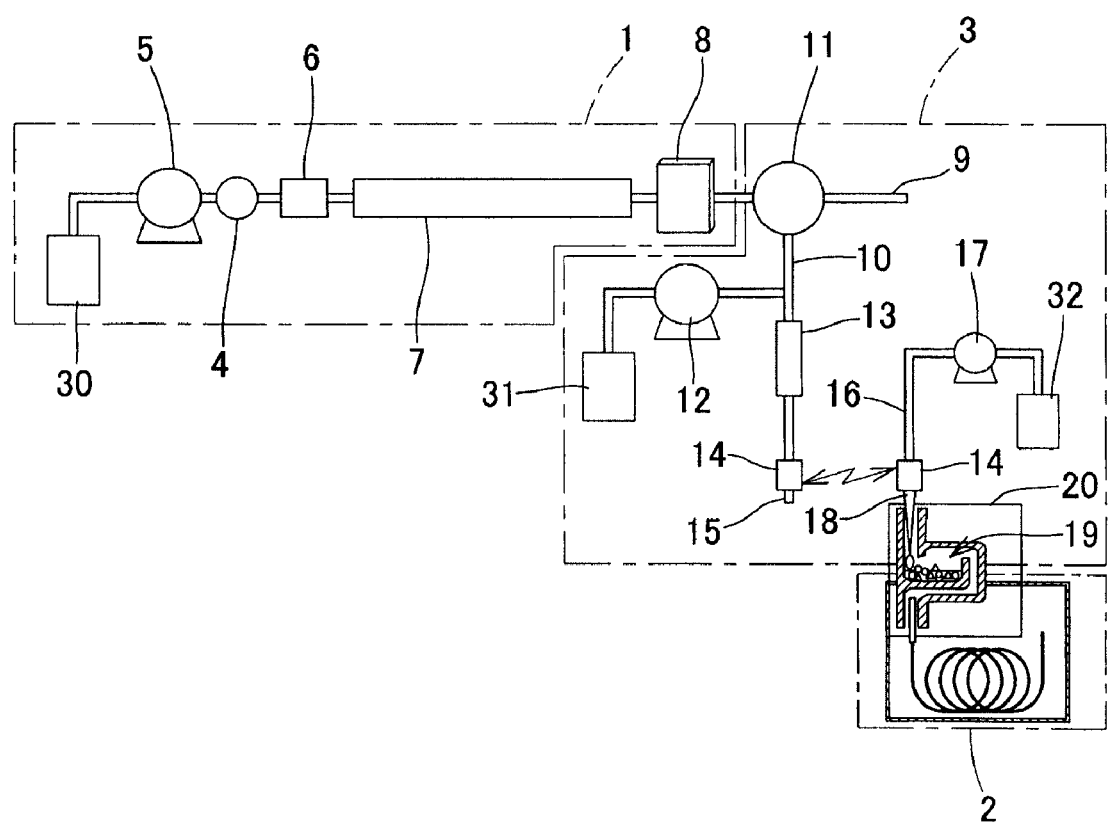
FIG. 1 is a schematic diagram of an apparatus for analysis.

1 Liquid chromatograph
2 Gas chromatograph
3 Interface
4 Inlet
5 Pump
6 Pre-column
7 LC column
8 Detector
9 Exhaust pathway
10 A first pathway
11 Valve
12 Pump
13 Mixer
14 Solid-phase cartridge
15 Outlet
16, 16A, A second pathway
17, 17A, A second pump
18, 18A, Syringe needle
19, 19A, Storage chamber
20, 20A, Vaporizing chamber
21A Peak of etoprophos
21B Peak of chloropyrifos
22 Switching valve
22A, 22B, 22C Passage
23-27 Solid-phase cartridge
28 Cartridge holder
30, 31,32, 32A Source/Reservoir

BEST MODE FOR CARRYING OUT THE INVENTION

The term of organic chemical substance in the present invention means an organic chemical substance including residual agricultural chemicals, endocrine disturbing chemicals, perfumes and the like, however it is not particularly limited thereto. As an agricultural chemical, the example can include asulam, oxine-copper, mecoprop, thiuram, siduron, iprodione, chlorothalonil, pencycuron, bensulide, chloropyrifos, and etoprophos. As endocrine disturbing chemicals, the example can include phenols such as nonylphenol and bisphenol A, phthalate, PCB, dioxins, organic tin compounds such as tributyl tin and triphenyl tin, and synthesized estrogen such as ethyl estradiol and estriol. As a perfume, the example can include limonene, dipentene, terpinolene, allo-ocimene, ocimene, linalool, geraniol, neol, citronelol, and mugol.

The term analysis target sample in the present invention is not particularly limited, includes a sample of the object to be analyzed such as an organic chemical substance included as a component of vegetable food and animal food, and an organic chemical substance adhering to the surface of foods. For example, vegetables are suitable as a target sample to be analyzed for residual agricultural chemicals or endocrine disturbing chemicals adhering to the surface of the vegetables.

A sample for analysis to be introduced to a liquid chromatograph is prepared by extracting organic chemical substances with a solvent with its concentration being adjusted. For example, water is added to sliced vegetables and fruits, or ground grains and beans to make them sufficiently swollen, followed by homogenization with a solvent such as acetonitrile, acetone, methanol, ether, or water, and then organic chemical substances are extracted by filtering. This extract of organic chemical substances is a sample for analysis.

The term analysis target substance in the present invention means an organic chemical substance contained in a target sample and a target substance whose content is to be analyzed. In the present invention, the sort of analysis target substance is not particularly limited, but it is desirable for a precise and speedy analysis that the sort is of from 1 to 20.

The term of derivatization reagent in the present invention means a reagent for enhancing analysis precision by obtaining the derivative of an analysis target substance using a derivatization reagent when an analysis target substance is analyzed as it is in a gas chromatograph to yield poor analysis precision. The example includes N,O-Bis(trimethylsilyl)trifluoroacetamide (BSTFA), Trimethylsilyl-diazomethane (TMS-Diazomethane), and the like.

Additionally, dirt can be removed by a solid-phase cartridge before a sample for analysis is fractionated by liquid chromatography. In this case, the sort of packing agent for a solid-phase cartridge can be changed according to the sort of dirt.

FIG. 1 shows a configuration of an apparatus for analysis where a liquid chromatograph 1 and a gas chromatograph 2 are connected via an interface 3.

The liquid chromatograph 1 is provided with a pump 5 for providing a solution from source/reservoir 30 to an inlet 4 for introducing a sample for analysis to a LC column, a pre-column 6 for removing dirt contained in the sample for analysis that deteriorates the LC column, a LC column 7 for separating an analysis target substance from dirt, and a detector 8 for detecting the analysis target substance containing an elute fractionated through the LC column 7.

The foregoing interface 3 is provided with a valve 11 for switching an exhaust address of elute containing the analysis target substance from the detector 8 to a first pathway 10 side of an exhaust pathway 9 side when detector 8 detects a desired analysis target substance; a first pump 12, having source/reservoir 31, as the first providing means for automatically providing a first solution different from a solution contained in the elute containing the analysis target substance introduced to the first pathway 10 side on the basis of an elution time of the analysis target substance, namely based on a switching signal of the valve 11; a mixer 13 for mixing the first solution from the first pump 12 and the elute from the valve 11; and a solid-phase cartridge 14 for adsorbing the analysis target substance out of the effluent from the mixer 13; and water and the like which was not adsorbed on the solid-phase cartridge 14 is exhausted through an outlet 15 below. The interface 3 is also provided with a second pump 17, having source/reservoir 31, as the second providing means for automatically providing an eluent for eluting the analysis target substance adsorbed on the solid-phase cartridge 14 to a second pathway 16 which is different from the first pathway 10.

The foregoing solid-phase cartridge 14 is configured in an attachable and detachable way to the first pathway 10 and in an attachable and detachable way to an end of the second pathway 16 as well. Therefore, the solid-phase cartridge 14 on which an analysis target substance has been adsorbed can be removed from the first pathway 10 and attached to the end of the second pathway 16. It is configured to elute the analysis target substance adsorbed on the solid-phase cartridge 14 so as to be introduced to the gas chromatograph 2 for analysis by activating the second pump 17 based on a detection signal by a detector such as a sensor in detecting the solid-phase cartridge 14 adsorbing the analysis target substance which was removed from the first pathway 10 and attached to the second pathway 16. In addition, it is possible, as a packing agent of solid-phase cartridge, to exemplify C18, C8, CN, diol, $NH_2$, alumina, florisil, silica, activated carbon, or the like.

A syringe needle 18 is connected to the outlet below the foregoing solid-phase cartridge 14, and the analysis target substance flowing out from the solid-phase cartridge 14 can be injected simply without loss via the syringe needle 18 by assembling the solid-phase cartridge 14 to the second pathway 16. In this case, a solution containing a derivatization reagent is injected into a storage chamber 19 together with the analysis target substance flowing out from solid-phase cartridge 14, and the analysis target substance can be derivatized in the storage chamber 19. The gas chromatograph 2 is configured with the storage chamber 19 capable of temporarily storing the analysis target substance introduced from the syringe needle 18 inside a vaporizing chamber 20.

Figure 2:
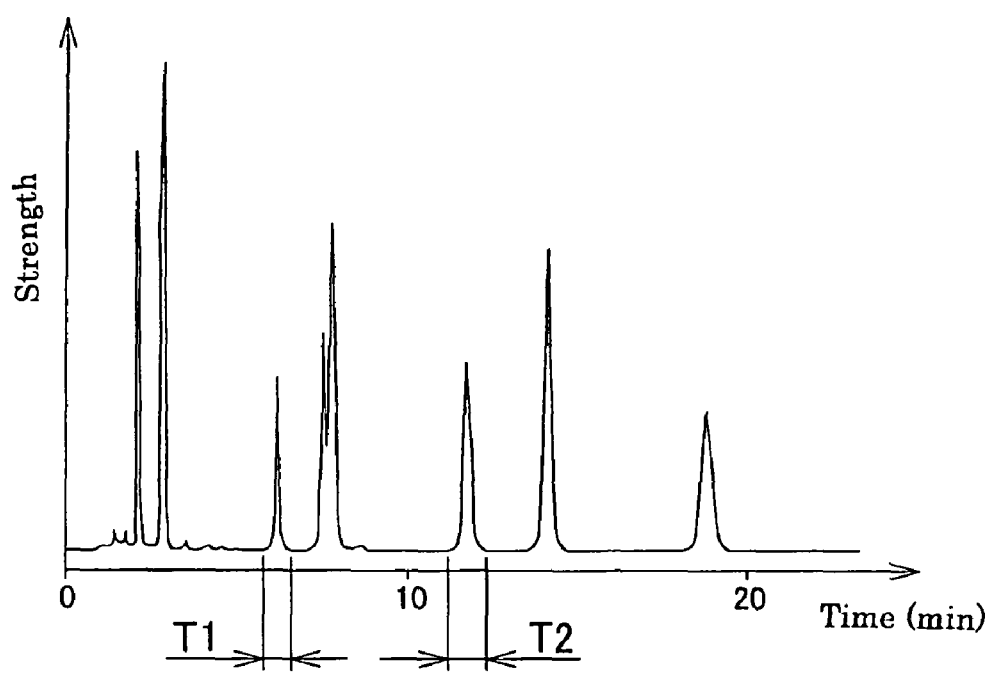
FIG. 2 is a chromatogram showing the detected result by a detector.

FIG. 2 shows a chromatogram depicting an eluting state of a sample for analysis injected from the inlet 4 caused by a solution from the pump 5 as a function of time. In the two points in FIG. 2, flow-out times of analysis target substances are shown, during the detection period of time detecting the flow-out by the detector 8, or during the time that an analysis target substance pre-examined is flowing out, it is controlled so as to switch the valve 11 in a flow-out state into the first pathway 10 by a control means.

Figure 5:
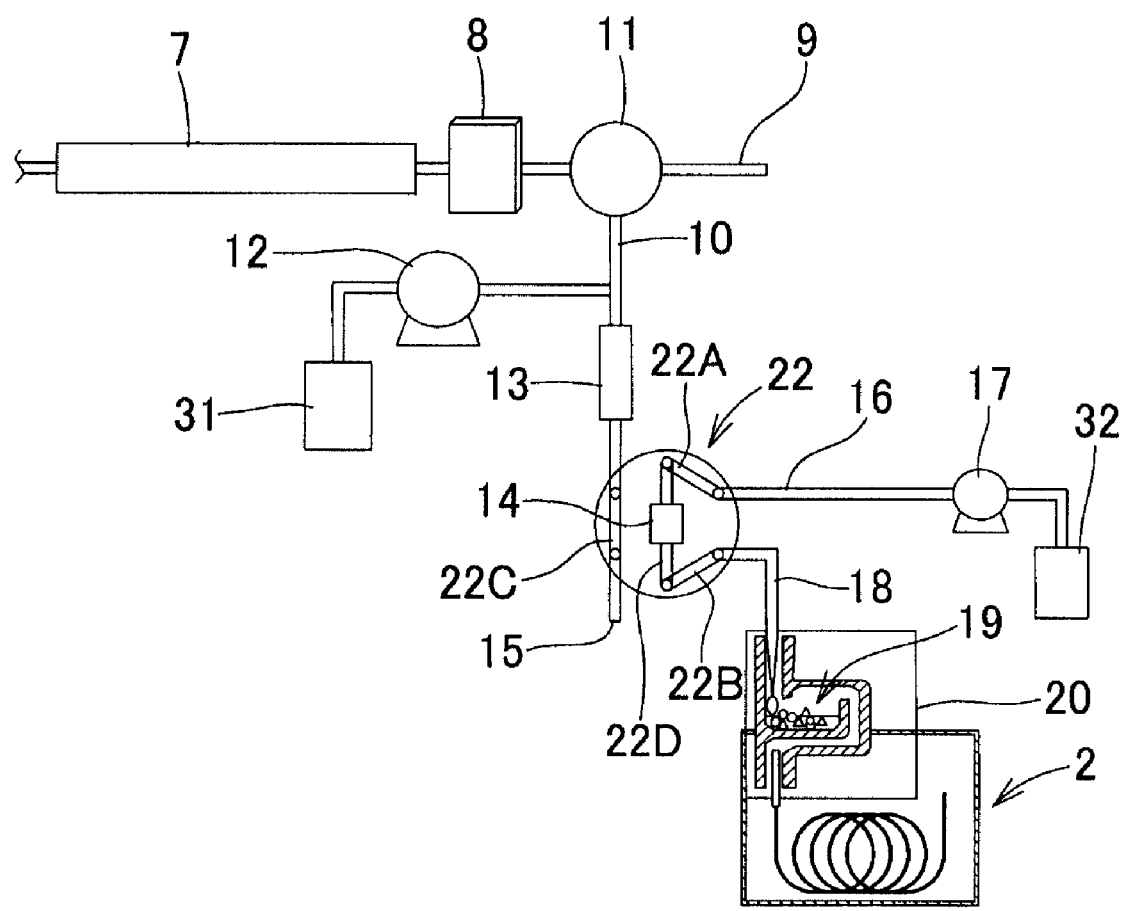
FIG. 5 is a schematic diagram of another apparatus for analysis capable of switching supply passage into a solid-phase cartridge by a switching valve.

Although the solid-phase cartridge 14 on which an analysis target substance is adsorbed is removed from the first pathway 10 and attached to the second pathway 16 in FIG. 1, it can be configured as shown in FIG. 5 to provide a switching valve 22 (a rotary valve is shown in the figure, but other sliding types for switching may be applied) at a point of the first pathway 10 joining the second pathway 16, and switch this switching valve 22 by hand or automatically so that the analysis target substance adsorbed on the solid-phase cartridge 14 can be provided to the gas chromatograph 2 without assembling and disassembling the solid-phase cartridge 14.

To be more specific, in a spool (omitting a sleeve as casing covering a spool outer periphery) of a moving side (rotating side) in the switching valve 22, there are formed a first passage 22A for taking in a first solution from the mixer 13 or an elute from the second pump 17 to flow to a providing passage 22D toward the solid-phase cartridge 14, a second passage 22C for providing an effluent from the first passage 22A to the outlet 15 side via a providing passage 22D, a third passage 22B for providing an analysis target substance flowing out from the providing passage 22D to a syringe needle 18 (gas chromatograph 2), so that a providing state can be switched as follows: a first providing state (see FIG. 6($a$)) wherein the analysis target substance transferred by the first solution is supplied to the solid-phase cartridge 14 via the first passage 22A and the supply passage 22D and adsorbed on the solid-phase cartridge 14, while water and the like which was not adsorbed is exhausted through the outlet 15 below via the second passage 22C; and a second providing state (see FIG. 5 and FIG. 6($b$)) wherein using the spool 22 by hand or electric power to turn it by 60 degrees toward the arrow direction in FIG. 6($a$), the eluent is supplied to the solid-phase cartridge 14 via the first passage 22A and the supply passage 22D, the analysis target substance adsorbed on the solid-phase cartridge 14 is eluted and introduced to the syringe needle 18 (gas chromatograph 2) via the third passage 22B. When the switching valve 22 is set in the second providing state, the syringe needle 18 is simultaneously moved downward to realize the state that the syringe needle 18 is inserted in the gas chromatograph 2. The second providing state shown in FIG. 6($b$) is returned to the first providing state by rotating the spool 22 by 60 degrees to the direction indicated by the arrow (reverse direction) shown in the figure. In this case, the solution containing a derivatization reagent is injected to the gas chromatograph 2 together with the analysis target substance flowing out from the solid-phase cartridge 14, and the analysis target substance can be derivatized in the storage chamber 19.

Figure 7:
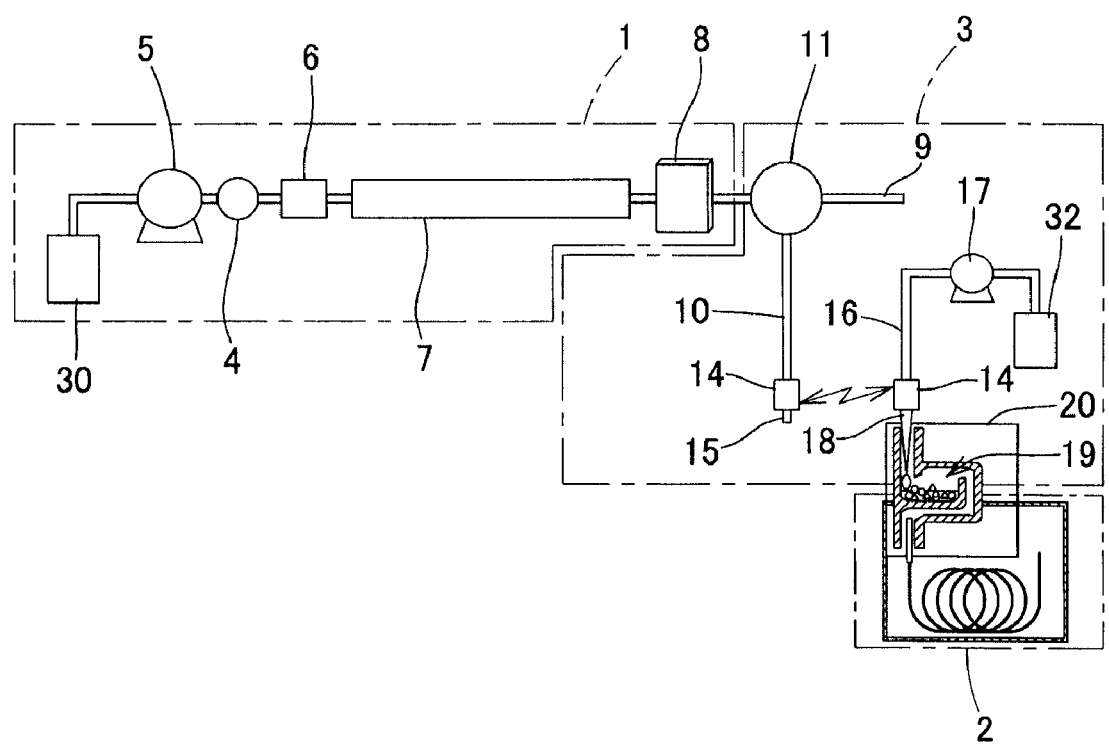
FIG. 7 is a schematic diagram of an apparatus for analysis where a second pump is omitted.

FIG. 1 shows a pump 12 provided for providing the first solution to the elute containing the analysis target substance fractionated by the liquid chromatograph 2, and FIG. 7 shows an apparatus for analysis that the first solution is not provided to the elute. The other parts without explanation are the same as those in FIG. 1.

Figure 8:
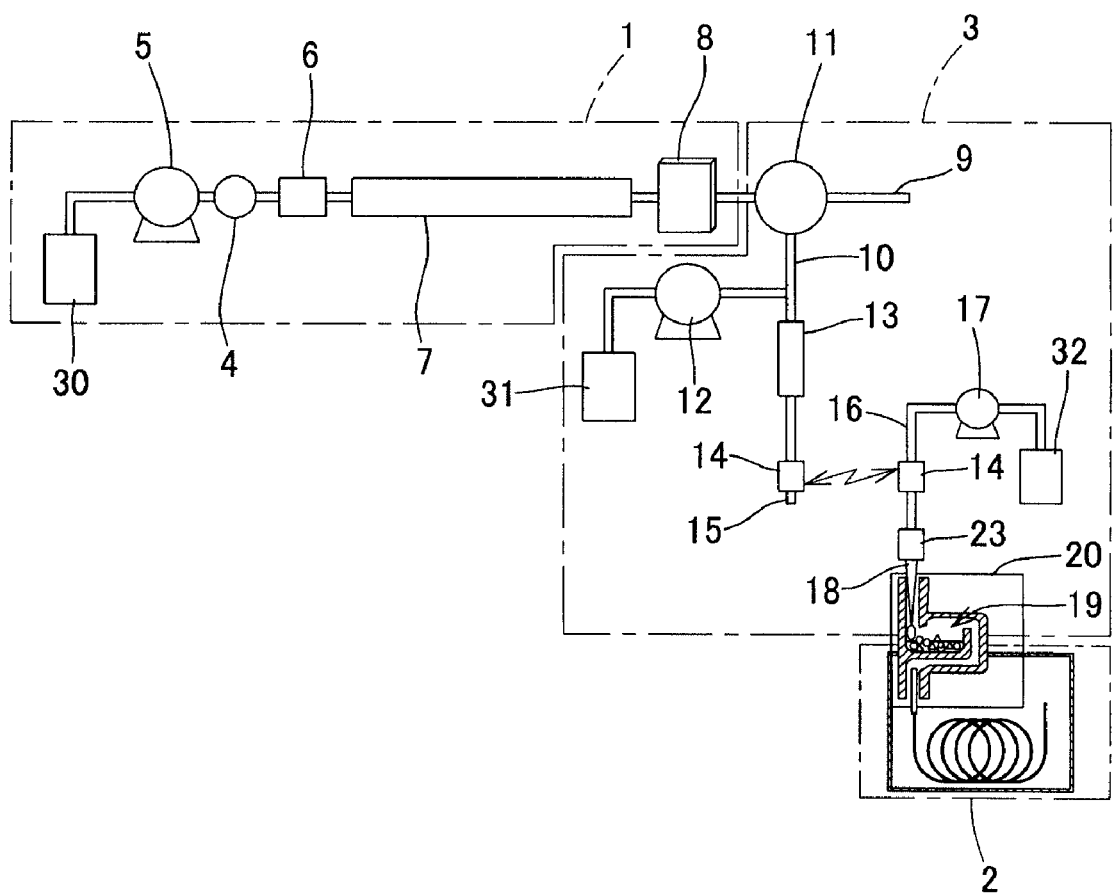
FIG. 8 is a schematic diagram of another apparatus for analysis that is provided with a solid-phase cartridge for a clean up.

As is shown in FIG. 8, a solid-phase cartridge 23 for removing dirt is provided at an exhaust side in the lower end of the solid-phase cartridge 14 in the second pathway 16 in order to adsorb dirt in an elute containing the analysis target substance eluted from the solid-phase cartridge 14. In this way, an analysis without pretreatment for cleaning up can be carried out, which gives a merit of shortening the analysis time. The other parts without explanation are the same as those in FIG. 1.

Figure 9:
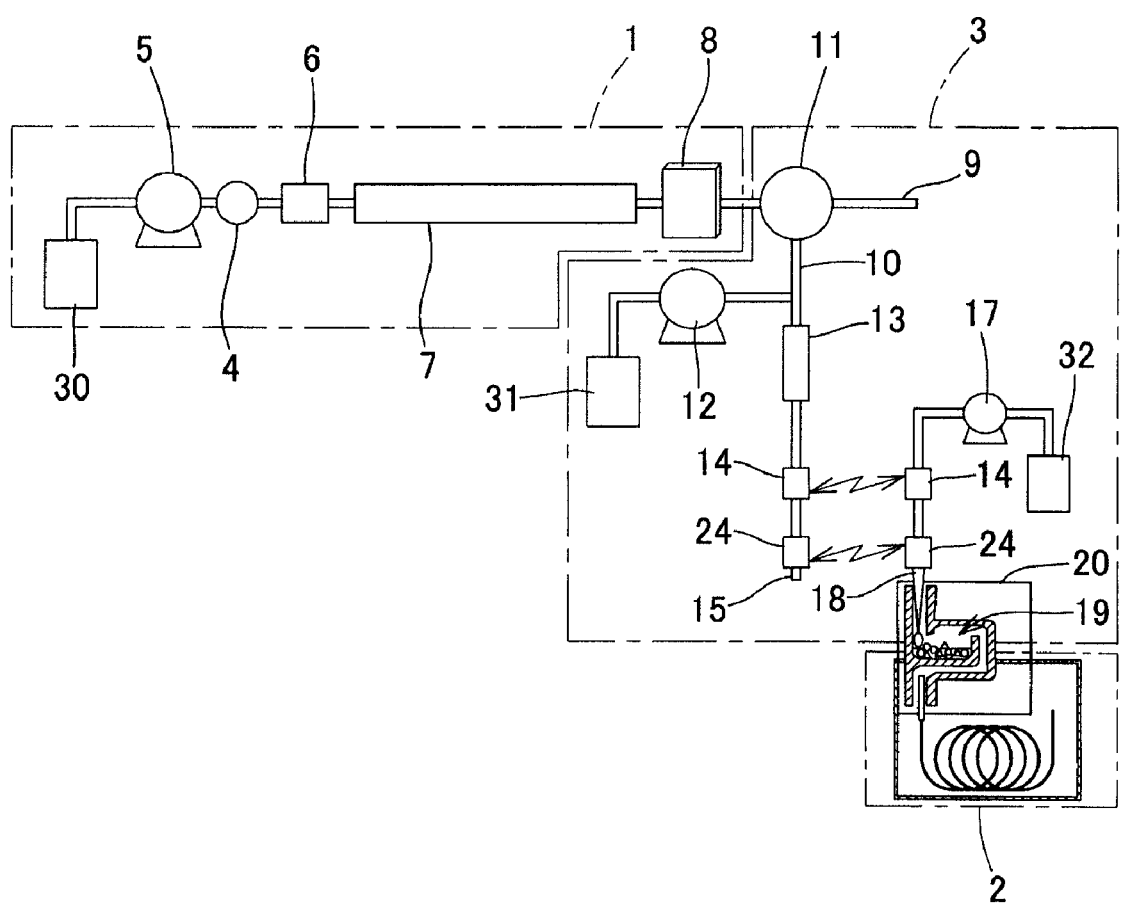
FIG. 9 is a schematic diagram of another apparatus for analysis that is provided with a plurality of solid-phase cartridges.

As is shown in FIG. 9, another solid-phase cartridge 24 with the identical configuration may be provided in an attachable and detachable way to the first pathway 10 in order to adsorb once again the analysis target substance that was not adsorbed by the solid-phase cartridge 14. FIG. 9 shows two other solid-phase cartridges 14 and 24, and solid-phase cartridges of three or more may be attached in an attachable and detachable way to the first pathway 10. Accordingly, after an analysis target substance is adsorbed by a plurality of solid-phase cartridges 14 and 24 (two in FIG. 8), the solid-phase cartridges 14 and 24 are removed and attached to the second pathway 16, by eluting the analysis target substance with an eluent, resulting in more analysis target substances being adsorbed compared with the case where adsorption is carried out by only one solid-phase cartridges 14, which realizes the reliable analysis. The other parts without explanation are the same as those in FIG. 1.

Figure 10:
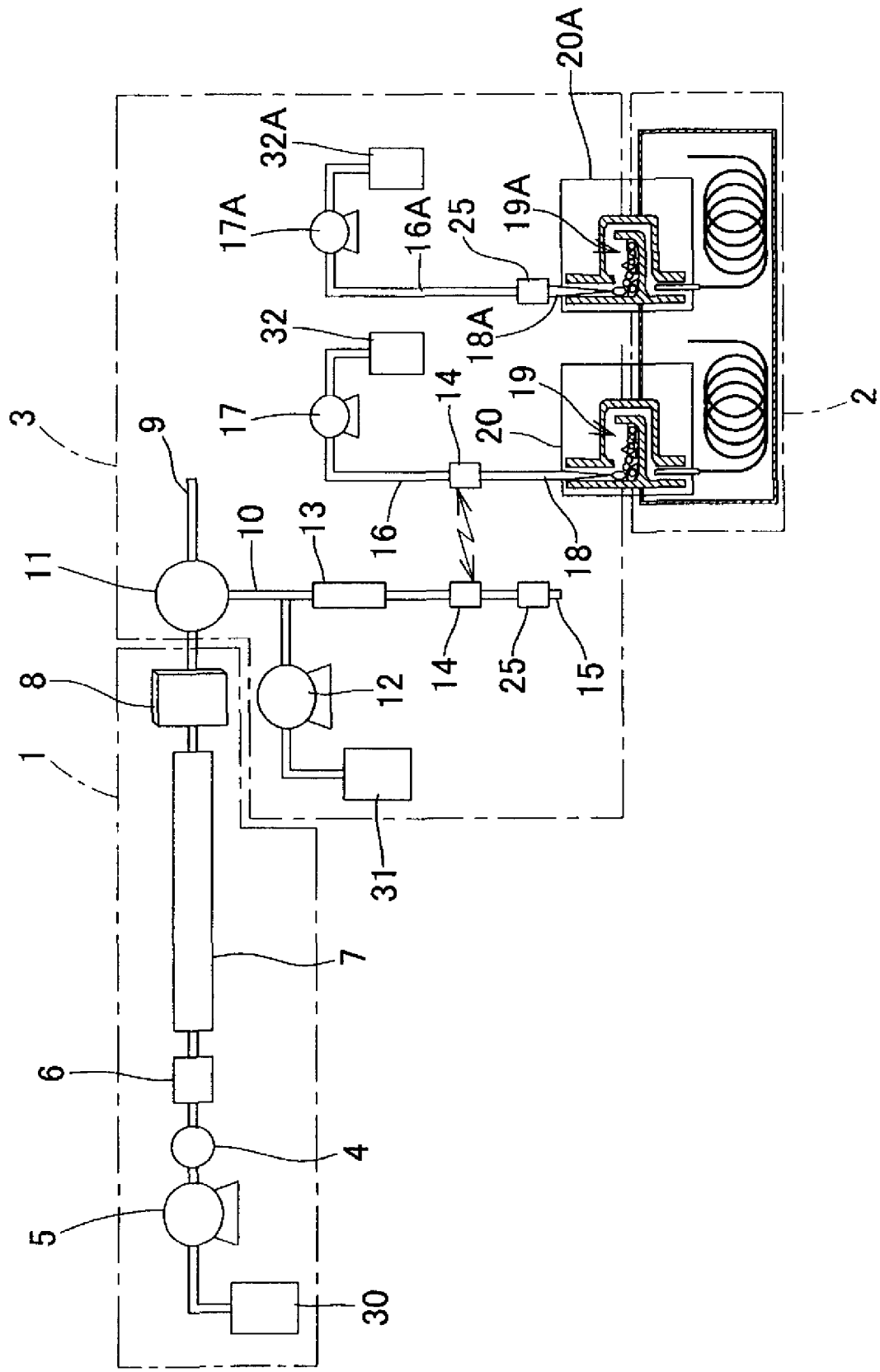
FIG. 10 is a schematic diagram of another apparatus for analysis that has a constitution capable of flowing out respective analysis target substances into two storage chambers.

As is shown in FIG. 10, a second solid-phase cartridge 25 may be attached in an attachable and detachable way to the first pathway 10 in order to adsorb other analysis target substances again that were not adsorbed by the solid-phase cartridge 14. The second pumps 17, 17A, each having source/reservoir 32, 32A respectively, are attached to the second pathways 16, 16A respectively for providing different eluents with respect to the solid-phase cartridges 14 and 25 that adsorbed the different two analysis target substances, eluting the different analysis target substances from each solid-phase cartridges 14, 25 and providing each elute to two different vaporizing chambers 20, 20A in order to analyze different analysis target substances at the same time. Although FIG. 10 shows two solid-phase cartridges 14, 24, solid-phase cartridges of three or more may be provided in order to analyze three or more analysis target substances. FIG. 10 shows the case where different vaporizing chambers 20, 20A are provided, however, by giving the time difference, analysis can be performed with the same vaporizing chamber where the different analysis target substances are to be eluted. The other parts without explanation are the same as those in FIG. 1.

Figure 11:
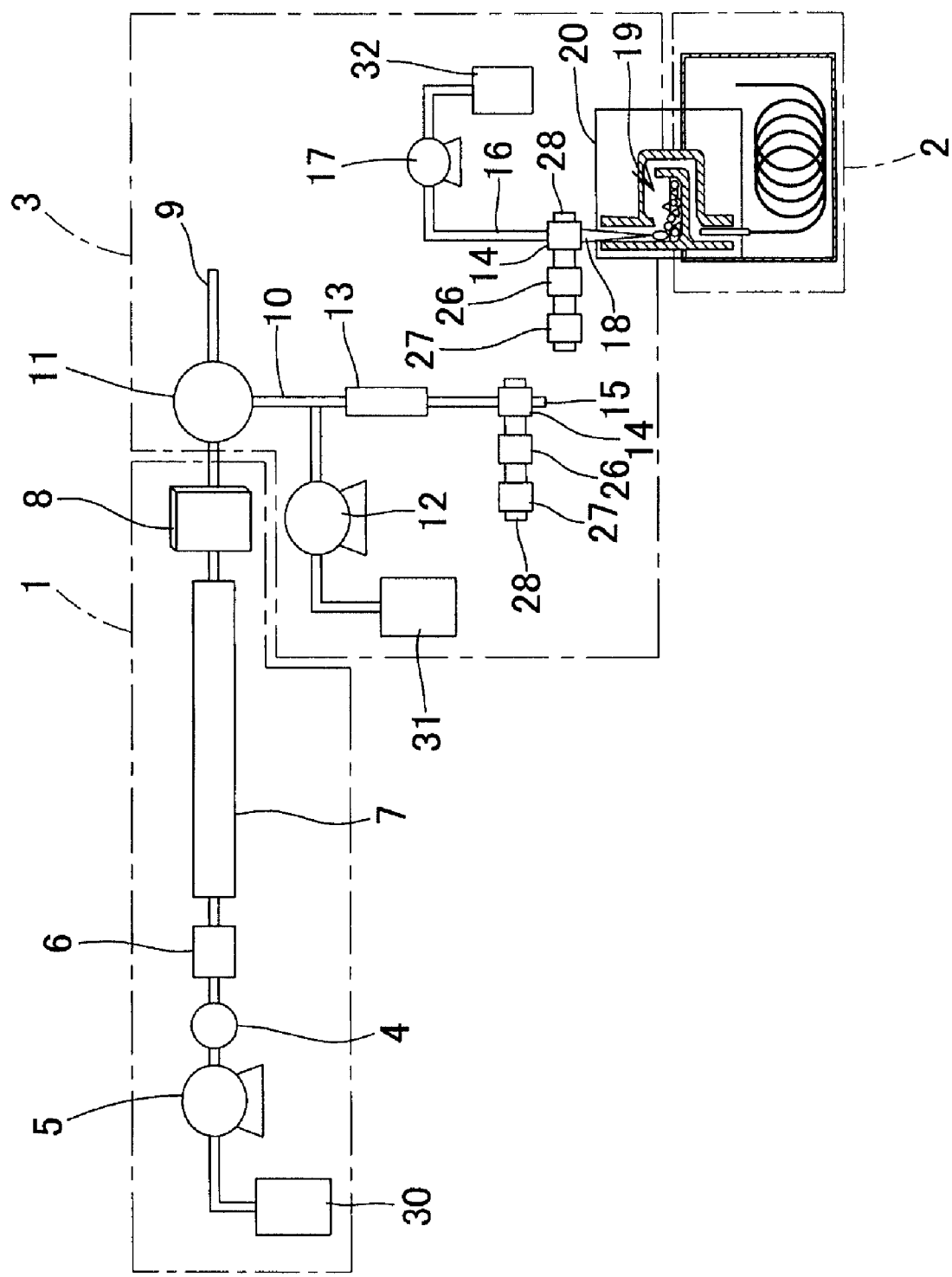
FIG. 11 is a schematic diagram of another apparatus for analysis where three solid-phase cartridges are held in a cartridge holder.

As is shown in FIG. 11, by providing a plurality of solid-phase cartridges 14, 26 and 27 (3 units in the figure, but 2 or more than 4 are applicable) in a cartridge holder 28, it can be devised to adsorb analysis target substances with a plurality of peaks by moving the cartridge holder 28 in the longitudinal direction by a driving mechanism such as an electric motor based on the timing (based on time passage or detection signal from a sensor) synchronized with the analysis target substance eluting at each peak of the analysis target substances having a plurality of peaks. Then, the cartridge holder 28 equipped with solid-phase cartridges 14, 26 and 27 which adsorbed analysis target substances is switched from the first pathway 10 into the second pathway 16, and by moving the cartridge holder 28 in the longitudinal direction using a driving mechanism like an electric motor, analysis target substances having a plurality of peaks can be analyzed. When different analysis target substances are adsorbed by the solid-phase cartridges 14, 26 and 27, a plurality of analysis target substances are analyzed by eluting with different eluents in different vaporizing chambers. Additionally, when an analysis target substance of the same kind is adsorbed by a plurality of solid-phase cartridges 14, 26 and 27, in a state that a plurality of solid-phase cartridges 14, 26 and 27 are placed in series to the second pathway 16, the analysis target substance is eluted by flowing an eluent from a single pump. The other portions not explained are the same as those in FIG. 1.

The solid-phase cartridge 14 shown in FIG. 1, FIG. 7 and FIG. 8 is depicted in a solid line in both the first pathway 10 and the second pathway 16. However, in practice, when it is in the first pathway 10, it is not in the second pathway 16, when it is in the second pathway 16, it is not in the first pathway 10. That is, the solid-phase cartridge 14 is in a state that it is connected to only one of the pathways. Additionally, in the cartridges 14, 24, 25, 26 and 27 shown in FIGS. 9 to 11, similarly the solid-phase cartridge 14 is in a state that it is connected to only one of the pathways (14 and 24 in FIGS. 9, 14 and 25 in FIGS. 10, 14, 26 and 27 in FIG. 11).

EXAMPLE 1

Figure 3:
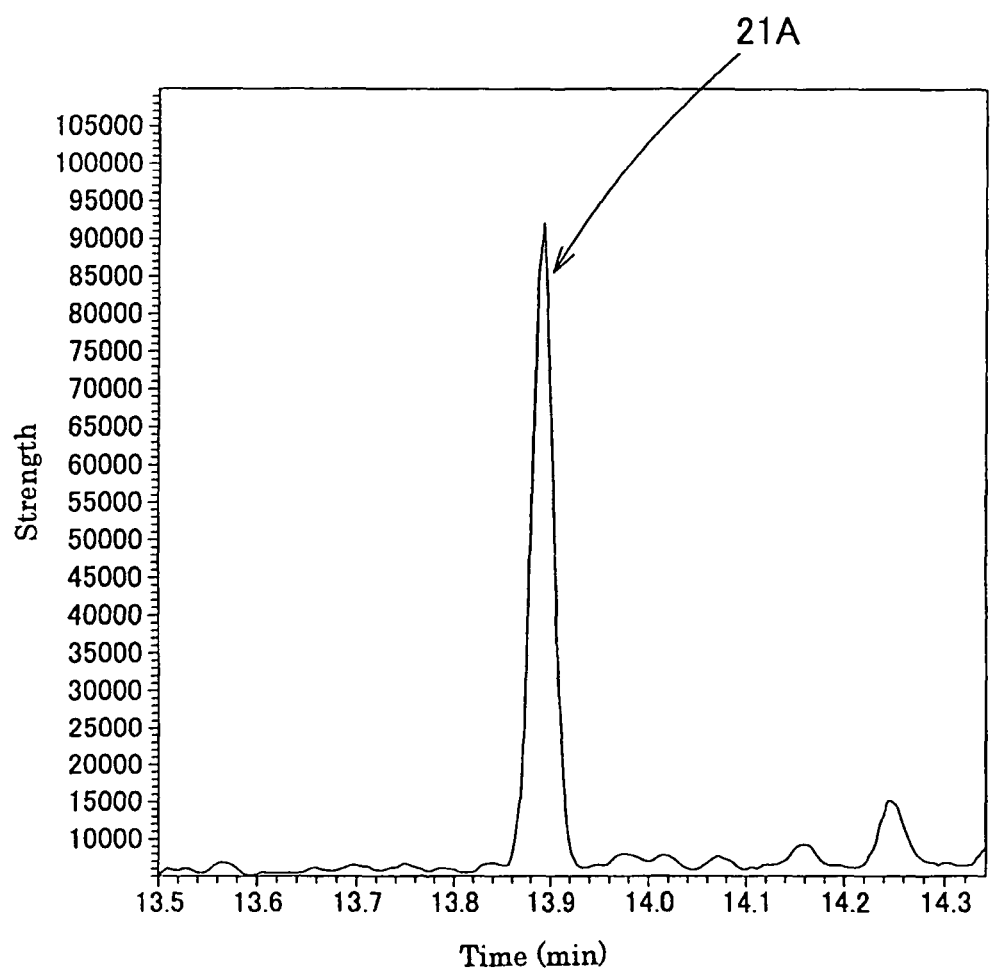
FIG. 3 is a chromatogram showing the result of an addition-recovery test.

Analysis of residual agricultural chemicals in spinach was performed by addition recovery test.
Preparation of Sample:
20 g of spinach was weighed, 100 ml of acetonitrile was added thereto, 0.02 mg of etoprophos was added, the mixture was homogenized and filtered under vacuum to obtain filtrate as a spinach extract.
Analysis Apparatus:
Liquid Chromatograph (HPLC)
Column: ODS 2.1×100 mm
Moving phase: 70% aqueous acetonitrile
Flow rate: 0.2 ml/min
Injection volume: 5 μl
Measurement wavelength: 254 nm
Gas Chromatograph (GC/MS)
Storage chamber: large injection type (use of craw-shaped lining)
Temperature of storage chamber: 60° C.-100° C./min-250° C. (20 min)
Temperature of column oven: 60° C. (4 min)-10° C./min-260° C. (5 min)
Interface:
Solid-phase cartridge: Solid-phase C18
Parting liquid: water, 2 ml/min
Eluent: acetone 50 μl
Analysis Method
10 μl of spinach extract is injected into the HPLC to separate by a liquid chromatograph. By switching a valve at the eluting time of etoprophos being examined beforehand, the elute was passed through a solid-phase cartridge while adding water. In this way, etoprophos is adsorbed on the solid-phase cartridge. A syringe was placed in the solid-phase cartridge, by eluting with acetone eluent directly into the storage chamber of a gas chromatograph to analyze by GC/MS. As a result, etoprophos with the recovery rate of 90% or more, and an excellent chromatogram shown in FIG. 3 were obtained. 21A in FIG. 3 shows a peak of etoprophos.

EXAMPLE 2

Figure 4:
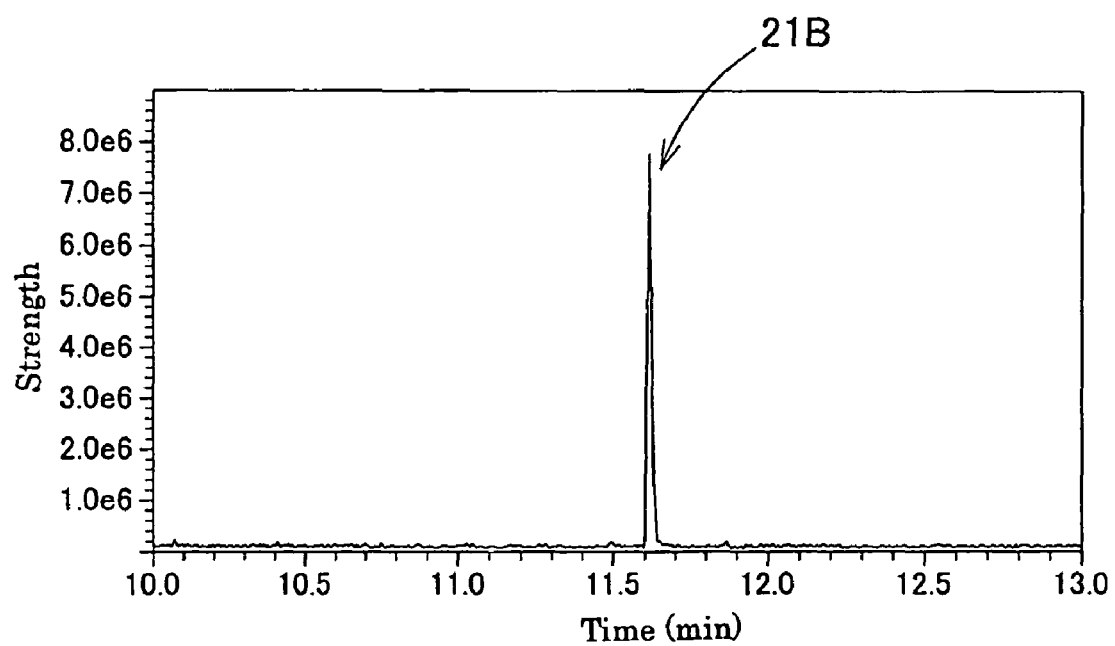
FIG. 4 is a chromatogram showing the result of another addition-recovery test.

Analysis of residual agricultural chemicals in spinach was performed by an addition recovery test.
Preparation of Sample:
20 g of spinach was weighed, 100 ml of acetonitrile was added thereto, 0.02 mg of chlorpyrifos was added, the mixture was homogenized and filtered under vacuum to obtain filtrate as a spinach extract.
Analysis Apparatus:
Liquid Chromatograph (HPLC)
Column: C2 3.0 mm i.d.×100 mm
Separation liquid: 50% aqueous acetonitrile
Flow rate: 0.5 ml/min
Injection volume: 100 μl
Measurement wavelength: 210 nm
Interface:
Solid-phase cartridge: solid-phase styrene-divinylbenzene
Eluent: hexane solution
Gas Chromatograph (GC/MS)
Storage chamber: large injection type (use of craw-shaped lining)
Temperature of storage chamber: 70° C.-120° C./min-220° C. (3 min)-50°/min-260° C. (10 min)
Temperature of column oven: 70° C. (3 min)-20° C./min-280° C. (4 min)
MS method: SCAN
Analysis Method:
100 μl of spinach extract is injected into the HPLC to separate by a liquid chromatograph. By switching a valve at the eluting time being beforehand examined of chlorpyrifos, the elute was passed through a solid-phase cartridge. In this way, chlorpyrifos is adsorbed on the solid-phase cartridge. A syringe was placed in the solid-phase cartridge, by eluting with hexane eluent directly into the storage chamber of a gas chromatograph to analyze by GC/MS. As a result, chlopyrifos of 90% or more recovery rate, and an excellent chromatogram shown in FIG. 4 were obtained. 21B in FIG. 4 shows a peak of chlorpyrifos.

EXAMPLE 3

Figure 12:
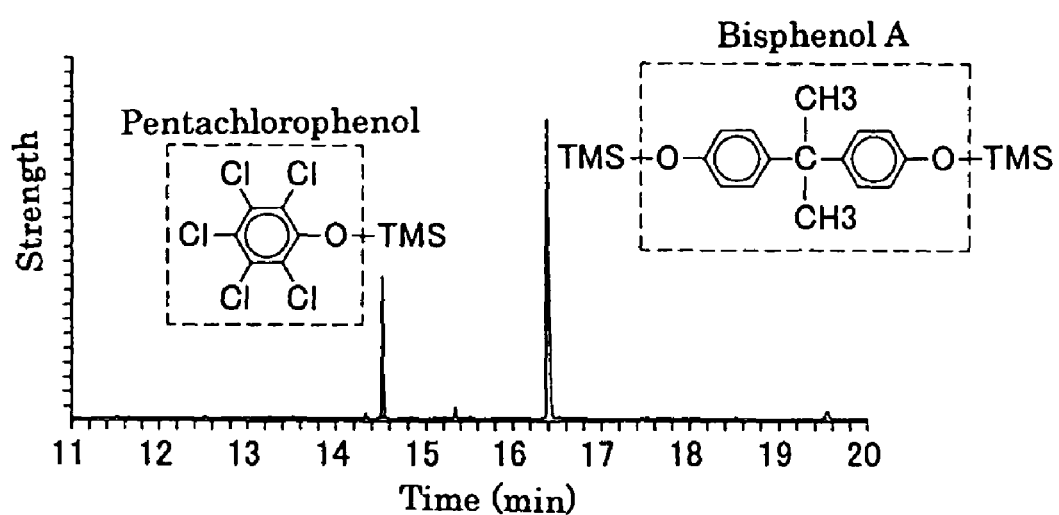
FIG. 12 is a chromatogram in the case of using a derivatization reagent.

By injecting a sample and a derivatization reagent consecutively into a storage chamber, derivatization was conducted in the storage chamber, and then analysis was performed.
Preparation of Sample and Derivatization Reagent:
As a sample, pentachlorophenol and bisphenol A diluted with acetone were used. As a derivatization reagent, N,O-Bis(trimethylsilyl)trifluoroacetamide (BSTFA) diluted with acetone was used.
Analysis Apparatus:
Gas Chromatograph (GC/MS)
Column: DS-5 ms, 0.25 mm i.d.×30 m, df=0.25 μm
Temperature of vaporizing chamber: 50° C.-30° C./min-180° C. (2 min)
Temperature of oven: 50° C. (5 min)-20° C./min-240° C. (4 min)
Carrier gas: He
Split initial flow rate: 30 ml/min
Splitless time: 5 min
Injection volume of sample: 2 μl
Injection volume of BSTFA: 1 μl
Analysis Method:
A sample is injected and maintained in a storage chamber 19 inside a vaporizing chamber 20. Next, a derivatization reagent (BSTFA) is injected into the vaporizing chamber 19. The temperature of the vaporizing chamber 20 is set at a proper temperature, derivatization is carried out while condensing. This derivative is introduced into a gas chromatograph. A chromatogram obtained by this analysis is shown in FIG. 12. The results show that the derivatization was surely conducted. Using this injection method of a derivatization reagent, there are merits that a pretreatment operation to be derivatized beforehand can be skipped, derivatization can also be done without touching a derivatization reagent which gives a bad influence on a human body, and analysis can be performed just after derivatization.

INDUSTRIAL APPLICABILITY

A method of analyzing organic chemical substances according to the present invention can measure specific residual agricultural chemicals and endocrine disturbing chemicals of one to about twenty sorts at high speed and also with high precision, which is suitable to evaluate the safety of target foods etc. quickly.

The invention claimed is:

1. A method of analyzing organic chemical substances comprising:
  subjecting a sample for analysis prepared beforehand by extracting organic chemical substances from a target sample to fractionation by a liquid chromatograph to obtain a fractionated elute;
  adding a, different from the elute, solution to said fractionated elute containing an analysis target substance;
  continuously adsorbing said analysis target substance onto a solid-phase cartridge from the liquid chromatograph; and
  eluting the analysis target substance which has been adsorbed on said solid-phase cartridge with an eluent directly into a storage chamber of a gas chromatograph to analyze by gas chromatography.

2. The method of analyzing organic chemical substances of claim 1, wherein on eluting the analysis target substance which has been adsorbed on said solid-phase cartridge with an eluent directly into a storage chamber of the gas chromatograph, a derivatization reagent is dissolved in said eluent, the resultant solution together with the analysis target substance is injected into the storage chamber of the gas chromatograph, after the analysis target substance is derivatized in the storage chamber, the derivative is analyzed by gas chromatography.

3. The method of analyzing organic chemical substances of claim 1, wherein the analysis target substance which has been adsorbed on said solid-phase cartridge is eluted with an eluent, said eluent is then passed through a separate solid-phase cartridge and an effluent with dirt having been removed is injected into the storage chamber of the gas chromatograph to be analyzed by a gas chromatography.

4. The method of analyzing organic chemical substances of claim 3, wherein on eluting the analysis target substance which has been adsorbed on said solid-phase cartridge with an eluent, passing said eluent through a separate solid-phase cartridge and injecting an effluent with dirt having been removed into a storage chamber of a gas chromatograph, a derivatization reagent is dissolved in said effluent, the resultant solution together with the analysis target substance is injected into the storage chamber of the gas chromatograph, after the analysis target substance is derivatized in the storage chamber, the derivative is analyzed by gas chromatography.

5. The method of analyzing organic chemical substances of claim 1, wherein said analysis target substance is from one sort to twenty sorts.

6. A method of analyzing organic chemical substances comprising:
  subjecting a sample for analysis prepared beforehand by extracting organic chemical substances from a target sample to fractionation by a liquid chromatograph to obtain a fractionated elute;
  passing said fractionated elute containing an analysis target substance through a solid-phase cartridge;
  continuously adsorbing said analysis target substance onto said solid-phase cartridge; and
  eluting the analysis target substance which has been adsorbed on said solid-phase cartridge with an eluent directly into a storage chamber of a gas chromatograph to be analyzed by gas chromatography.

7. The method of analyzing organic chemical substances of claim 2, wherein on eluting the analysis target substance which has been adsorbed on said solid-phase cartridge with an eluent directly into a storage chamber of a gas chromatograph, a derivatization reagent is dissolved in said eluent, the resultant solution together with the analysis target substance is injected into the storage chamber of the gas chromatograph, after the analysis target substance is derivatized in the storage chamber, the derivative is analyzed by gas chromatography.

8. The method of analyzing organic chemical substances of claim 2, wherein the analysis target substance which has been adsorbed on said solid-phase cartridge is eluted with an eluent, said eluent is then passed through a separate solid-phase cartridge and an effluent with dirt having been removed is injected into the storage chamber of the gas chromatograph to be analyzed by gas chromatography.

9. An apparatus for analyzing organic chemical substances comprising:
  a liquid chromatograph where a sample for analysis prepared by extracting organic chemical substances contained in a target sample is introduced for fractionation;
  a first providing means for automatically providing to an elute containing analysis target substance fractionated by the liquid chromatograph a first solution which is different from said elute based on an elution time of said analysis target substance;

a solid-phase cartridge for adsorbing the analysis target substance transferred by a mixed liquid of said first solution and the elute fractionated by the liquid chromatograph;

a second providing means for automatically providing an elute to elute the analysis target substance which has been adsorbed on the solid-phase cartridge; and a syringe needle connected to an exit of said solid-phase cartridge to introduce said eluted analysis target substance to a gas chromatograph.

10. The apparatus for analyzing organic chemical substances of claim 9, wherein besides a first pathway to adsorb the analysis target substance transferred by a mixed liquid of said first solution and the elute fractionated by the liquid chromatograph onto the solid-phase cartridge, a second pathway is separately provided to elute the analysis target substance which has been adsorbed on the solid-phase cartridge and introduce the same to said gas chromatograph; and said solid-phase cartridge can freely be assembled or disassembled with two pathways respectively.

11. The apparatus for analyzing organic chemical substances of claim 10, wherein a switching valve is provided to switch providing states into a first providing state for providing and adsorbing the analysis target substance transferred by a mixed liquid of said first solution and the elute fractionated by the liquid chromatograph onto said solid-phase cartridge, and into a second providing state for providing said eluent to said solid-phase cartridge to elute the analysis target substance which has been adsorbed on the solid-phase cartridge and introducing the same to said gas chromatograph.

12. The apparatus for analyzing organic chemical substances of claim 11, wherein said gas chromatograph is provided inside a vaporizing chamber with a storage chamber, containing no scavenger, capable of temporarily storing the analysis target substance introduced from said syringe needle.

13. The apparatus for analyzing organic chemical substances of claim 10, wherein said gas chromatograph is provided inside a vaporizing chamber with a storage chamber, containing no scavenger, capable of temporarily storing the analysis target substance introduced from said syringe needle.

14. The apparatus for analyzing organic chemical substances of claim 9, wherein said gas chromatograph is provided inside a vaporizing chamber with a storage chamber, containing no scavenger, capable of temporarily storing the analysis target substance introduced from said syringe needle.

15. An apparatus for analyzing organic chemical substances comprising:

a liquid chromatograph where a sample for analysis prepared by extracting organic chemical substances contained in a target sample is introduced for fractionation;

a detecting means for detecting the transferred analysis target substance fractionated by the liquid chromatograph;

an exhaust address switching valve for switching an exhaust address from an exhaust pathway side into a main pathway side based on a detected signal for the analysis target substance by the detecting means;

a solid-phase cartridge provided in said main pathway to adsorb the analysis target substance transferred together with an elute being switched into the main pathway by said exhaust address switching valve;

a providing means for providing an eluent to introduce the analysis target substance which has been adsorbed on said solid-phase cartridge into the gas chromatograph; and a syringe needle capable of moving up and down connected to the exit of said solid-phase cartridge to introduce the analysis target substance eluted together with said eluent to a gas chromatograph.

16. The apparatus for analyzing organic chemical substances of claim 15, wherein besides the first pathway to adsorb the analysis target substance transferred together with said elute onto said cartridge, a second pathway is separately provided where the analysis target substance which has been adsorbed on said solid-phase cartridge is eluted with the eluent introduced from the providing means, to be introduced into the gas chromatograph, and said solid-phase cartridge capable of being freely assembled and disassembled with the two pathways respectively.

17. The apparatus for analyzing organic chemical substances of claim 16, wherein said gas chromatograph is provided inside a vaporizing chamber, with a storage chamber containing no scavenger, capable of temporarily storing the analysis target substance introduced from said syringe needle, inside the vaporizing chamber.

18. The apparatus for analyzing organic chemical substances of claim 15, wherein the providing state switching valve is provided for the providing state into the first providing state to supply and adsorb the analysis target substance transferred together with said elute onto said solid-phase cartridge, and into the second providing state to supply said eluent to said solid-phase cartridge to elute the analysis target substance which has been adsorbed on said solid-phase cartridge and introduce to said gas chromatograph.

19. The apparatus for analyzing organic chemical substances of claim 18, wherein said gas chromatograph is provided inside a vaporizing chamber, with a storage chamber, containing no scavenger, capable of temporarily storing the analysis target substance introduced from said syringe needle, inside the vaporizing chamber.

20. The apparatus for analyzing organic chemical substances of claim 15, wherein said gas chromatograph is provided inside a vaporizing chamber, with a storage chamber, containing no scavenger, capable of temporarily storing the analysis target substance introduced from said syringe needle, inside a vaporizing chamber.

* * * * *